(12) United States Patent
Abelson et al.

(10) Patent No.: US 8,748,402 B2
(45) Date of Patent: *Jun. 10, 2014

(54) OPHTHALMIC FORMULATIONS AND USES THEREOF

(75) Inventors: Mark Abelson, Andover, MA (US); Kirk McMullin, Villa Park, CA (US); Angel Padilla, Aliso Viejo, CA (US)

(73) Assignee: Bausch & Lomb Pharma Holdings Corp., Rochester, NY (US)

( * ) Notice: Subject to any disclaimer, the term of this patent is extended or adjusted under 35 U.S.C. 154(b) by 59 days.

This patent is subject to a terminal disclaimer.

(21) Appl. No.: 13/369,452

(22) Filed: Feb. 9, 2012

(65) Prior Publication Data
US 2012/0195972 A1 Aug. 2, 2012

Related U.S. Application Data

(63) Continuation-in-part of application No. 11/146,652, filed on Jun. 7, 2005, now Pat. No. 8,372,814.

(60) Provisional application No. 60/675,179, filed on Apr. 26, 2005, provisional application No. 60/577,567, filed on Jun. 7, 2004.

(51) Int. Cl.
*A01N 43/04* (2006.01)
*A61K 31/70* (2006.01)
*A61K 9/48* (2006.01)

(52) U.S. Cl.
CPC ........................................ *A61K 9/48* (2013.01)
USPC ............................................. 514/40; 514/178

(58) Field of Classification Search
CPC ....................................................... A61K 9/48
USPC .................................................. 514/40, 178
See application file for complete search history.

(56) References Cited

U.S. PATENT DOCUMENTS

| | | | |
|---|---|---|---|
| 4,134,403 A | 1/1979 | Johnson et al. | |
| 4,315,024 A | 2/1982 | Abelson | |
| 4,981,871 A | 1/1991 | Abelson | |
| 5,290,781 A | 3/1994 | Espino et al. | |
| 5,340,572 A | 8/1994 | Patel et al. | |
| 5,403,598 A | 4/1995 | Beck et al. | |
| 5,407,669 A | 4/1995 | Lindstrom et al. | |
| 5,475,034 A | 12/1995 | Yanni et al. | |
| 5,624,893 A | 4/1997 | Yanni | |
| 5,767,105 A | 6/1998 | Peyman | |
| 5,811,446 A | 9/1998 | Thomas | |
| 5,929,111 A | 7/1999 | Conrow et al. | |
| 6,117,907 A | 9/2000 | Sher | |
| 6,432,934 B1 | 8/2002 | Gilbard | |
| 6,465,506 B2 | 10/2002 | Abelson et al. | |
| 6,482,799 B1 | 11/2002 | Tusé et al. | |
| 6,599,891 B2 | 7/2003 | North et al. | |
| 6,624,193 B1 | 9/2003 | Naka et al. | |
| 6,646,001 B2 | 11/2003 | Hellberg et al. | |
| 6,699,493 B2 | 3/2004 | Wong | |
| 2004/0072809 A1 | 4/2004 | Demopulos et al. | |
| 2004/0077562 A1 | 4/2004 | Chandavarkar et al. | |
| 2006/0183698 A1 | 8/2006 | Abelson | |
| 2007/0254841 A1 | 11/2007 | Ousler et al. | |

FOREIGN PATENT DOCUMENTS

WO  WO 02/49614  6/2002

OTHER PUBLICATIONS

Tsubota et al (Progress in Retinal and Eye Research vol. 17, No. 4, pp. 565 to 596, 1998).*
International Search Report and Written Opinion issued by the World Intellectual Property Office, dated Dec. 20, 2006.
International Preliminary Report on Patentability issued by the World Intellectual Property Office, dated Oct. 30, 2007.
www.ou.edu, Buffers, available Apr. 7, 2004, printed from http://www.ou.edu/research/electron/bmz5364/buffers.html.
The Roberts Lab Group, SB (Sodium Borate) Buffer, 20x, printed from http://mmadisplay.usc.edu/lab/protocols/per/sb-sodium-borate-buffer-20x on May 22, 2010.
www.teknova.com, 10x Borate Saline Buffer, printed from http://www.teknova.com/product-p/b0230.htm May 22, 2010.
Tananuvat et al. Controlled Study of the Use of Autologous Serum in Dry Eye Patients, Cornea vol. 20, No. 8 (2001), pp. 802-806.
Engel et al, "Effectiveness of Specific Antibiotic/Steroid Combinations for Therapy of Experimental *Pseudomonas aerugionos* Keratitis" Current Eye Research, vol. 4, No. 3 (1995), pp. 229-234.
Van Haeringen, "Clinical Biochemistry of Tears" Survey of Ophthamology, vol. 26, No. 2 (1991), pp. 84-96.

* cited by examiner

*Primary Examiner* — Benjamin Packard
(74) *Attorney, Agent, or Firm* — Thompson Hine LLP

(57) ABSTRACT

Provided by the present invention are compositions or formulations suitable for application to a patient's eyes which utilizes a topical ophthalmically-acceptable formulation comprising a therapeutically-effective amount of an ophthalmically-active antimicrobial agent, and an ophthalmically-active anti-inflammatory or steroidal agent in combination with physiologic levels of serum electrolytes in an ophthalmic formulation for the treatment of changes in the normal eye condition. The invention also includes methods of treating patient's having an ophthalmic disease, injury or disorder, utilizing the compositions or formulations. Also provided are kits comprising the compositions or formulations and a means of applying the compositions or formulation to the patient's eyes.

32 Claims, No Drawings

OPHTHALMIC FORMULATIONS AND USES THEREOF

CROSS-REFERENCES TO RELATED APPLICATIONS

This application is a continuation in part of co-pending application Ser. No. 11/146,652, filed Jun. 7, 2005, which claims priority from U.S. Provisional Patent Applications 60/577,567 filed Jun. 7, 2004, and 60/675,179 filed Apr. 26, 2005, each of which is expressly incorporated by reference herein in its entirety.

BACKGROUND OF THE INVENTION

The present invention relates to ophthalmic formulations, kits and uses thereof, wherein the formulations utilize physiologic levels of serum electrolytes in conjunction with pharmacologically effective doses of an antimicrobial agent, and an anti-inflammatory or steroidal agent in a single formulation for the treatment of ocular disorders, diseases or injuries.

Combinations or formulations containing an antimicrobial agent and an anti-inflammatory agent are available in the ophthalmic art. However, there are concerns and expressed reservations in the ophthalmic community about the safety and efficacy of such prior art combinations. There continues to be a need for an effective and safe topical ophthalmic pharmaceutical composition of a steroid or anti-inflammatory agent and a broad spectrum antibiotic which, when administered to the eye will not inhibit the activity of the antibiotic, or steroidal or anti-inflammatory components.

Many ophthalmic conditions result in an aberrant tear film composition. The electrolyte balances and concentrations in tears can change as a result of a disruption in the normal eye physiology. For example, when ocular tissue is inflamed, serum components leak from the vasculature into the tear film. Many of these ophthalmic conditions are typically treated with antimicrobial and/or steroidal or anti-inflammatory compounds.

SUMMARY OF THE INVENTION

The present invention comprises a formulation which mimics the serum components of the injured eye (instead of the normal eye tear physiology) which when used in conjunction with an antimicrobial, and anti-inflammatory or steroidal agent in a single formulation assist in restoring the injured eye to its normal condition (i.e., non-inflamed and non-infected state).

The present invention utilizes physiologic levels of various serum electrolytes in an ophthalmic composition or formulation also containing an antimicrobial agent, and an anti-inflammatory or steroidal agent for the treatment of various ophthalmic injuries, diseases or disorders. Typically, the injury, disease or disorder results in an inflammatory response in and around the eye and/or causes leakage of the blood vessels in the eye. The serum electrolytes include sodium, potassium, chloride, calcium, magnesium, phosphate, and/or bicarbonate in concentrations to match the normal physiologic levels. These levels comprise sodium in a concentration from about 3105 to about 3358 mg/L; potassium in a concentration from about 136.85 to about 207.23 mg/L; chloride in a concentration from about 3368.7 to about 3829.68 mg/L; calcium in a concentration from about 85 to about 103 mg/L; magnesium in a concentration from about 14.592 to about 24.32 mg/L; phosphate in a concentration from about 85 to about 150 mg/L, and bicarbonate in a concentration from about 1281 to about 2013 mg/L.

The antimicrobial agent, and anti-inflammatory or steroidal agent of the composition or formulation are used to treat or mitigate the injury, disease or disorder. One steroidal agent contemplated in the present invention is prednisolone whereas a contemplated antimicrobial is tobramycin.

The invention also includes methods of treating patient's having an ophthalmic disease, injury or disorder, utilizing the compositions or formulations. Further, the compositions or formulations can be utilized to restore the normal condition of the eye when the normal condition has been disrupted or changed. Also provided are kits comprising the compositions or formulations and a means of applying the compositions or formulation to the patient's eyes.

DESCRIPTION OF THE INVENTION

Without being bound by a particular theory, it appears that the physiology of the injured or diseased eye more closely resembles the physiology of serum due to the release of vessel contents into the tear film and, as such, the contents are pathological to the condition of the eye. Therefore, the application of an ophthalmic formulation that mimics the injured eye condition is a focus of the present invention, since the application of such a formulation does not shock the already overly-sensitized tissues and is able to gradually restore the eye to a normal condition (i.e. non-inflamed and non-infected state). Such an approach is counterintuitive to conventional therapies, since physicians presently would not use a formulation that continues the pathologic condition within the eye. Nevertheless, it is important to consider that the addition of a formulation with electrolytes in "equilibrium" with the electrolytes in the "inflamed" eye may provide several advantages when used in conjunction with an antimicrobial and a steroidal or anti-inflammatory agent. Such advantages could include, but are not necessarily limited to, a formulation that is more comfortable to the patient which may result in better patient compliance and/or a formulation that promotes faster healing.

Definitions

"Ophthalmically-acceptable" means that the formulation, active agent, excipient or other material is compatible with ocular tissue; that is, it does not cause significant or undue detrimental effects when brought into contact with ocular tissue. In some instances, actives and/or excipients of the formulation may cause some discomfort or stinging in the eye; however, those excipients are still considered ophthalmically-acceptable for the purposes of this application. In many instances, these irritating components are removed from the formulations for comfort of the patient. For example, polyvinyl alcohol (PVA) can be eliminated from the formulation ingredients.

"Antimicrobial compound" includes those that effectively kill or mitigate the activity of a microbe. Antimicrobial includes antibacterial, bacteriostatic, and the like. These agents include, but are not limited to: azithromycin, tobramycin, gentamicin, ciprofloxacin, norfloxacin, ofloxacin, and sparfloxacin.

"Immunosuppressive agent," and "immunosuppressive drug," refers to any agent which inhibits or prevents an immune response. Exemplary agents include, but are not limited to: dexamethasone, cyclosporin A, azathioprine, brequinar, gusperimus, 6-mercaptopurine, mizoribine, rapamycin, tacrolimus (FK-506), folic acid analogs (e.g. denopterin, edatrexate, methotrexate, piritrexim, pteropterin, Tomudex®, trimetrexate), purine analogs (e.g., cladribine, fludarabine, 6-mercaptopurine, thiamiprine, thiaguanine), pyrimidine analogs (e.g., ancitabine, azacitidine, 6-azauridine, carmofur, cytarabine, doxifluridine, emitefur, enocitabine, floxuridine, fluorouracil, gemcitabine, tegafur), fluocinolone, triamcinolone, anecortave acetate, fluromethalone, medrysone, and prednisilone.

"Nutrient sugar" means any sugar that can provide nutrients to cells.

"Therapeutically-effective amount" means an amount of active sufficient to prevent, inhibit, or reduce the level of inflammation, irritation or other abnormal conditions in the eye.

"Derivative" means any analogs, salts, esters, amines, amides, acids and/or alcohols derived from an active agent of the invention which may be used in place of that active agent.

A "patient" is a vertebrate, preferably mammal, more preferably a human. Mammals include, but are not limited to: humans, rodents, sport animals and pets, such as rats, dogs, and horses.

"Ocular inflammation" includes, but is not limited to: inflammatory conditions of the palpebral and bulbar conjunctiva, cornea and anterior segment of the globe.

"Eye surface inflammation" includes any inflammatory disorder involving the ocular surface. The eye surface includes the eye lids, conjunctiva and cornea. "Inflammation" refers to white blood cell or leukocytic infiltration associated with cellular injury. Eye surface inflammatory disorders treatable by the ophthalmic preparations of the invention are typically manifested by signs and symptoms such as eye redness, or irritation. These diseases include, for example, meibomianitis, blepharitis conjunctival hyperemia, eyelid hyperemia, keratitis and ocular rosacea. The inflammation of tissue associated with the eye can be the result of a number of different causes. Whether the cause is bacterial, viral, traumatic, iatrogenic or environmental, inflammation can be painful, damaging to tissues and requires special care.

"Eye surface dryness" includes, but is not limited to: any ocular disorder resulting in loss of water or volume from the tear film. Such disorders generally can be characterized by increased tear film osmolarity and decreased levels of corneal glycogen and conjunctival mucus-containing goblet cells. Eye surface dryness can result from a number of different diseases but is not limited to: meibomian gland dysfunction and meibomian gland orifice stenosis or closure.

"Ocular infection" is an abnormal condition caused by bacteria, fungi and viruses. Infections, if not treated, can lead to more severe ocular disorders.

"Corneal opacification" consists of a clouding or scarring of the normally transparent cornea, that diminishes the amount of light entering the eye, impairing vision. Corneal opacification can occur as a result of bacterial, fungal or viral infections, or from trauma to the eye.

"Diabetic retinopathy" is a complication of diabetes typically classified into two stages, Non-Proliferative Diabetic Retinopathy (NPDR) and Proliferative Diabetic Retinopathy (PDR).

"Non-Proliferative Diabetic Retinopathy" (NPDR) is a complication of diabetes in the early stage of diabetic retinopathy that occurs when normal blood vessels in the retina are damaged due to diabetes and swell and begin to leak fluid and small amounts of blood into the eye.

Serum Electrolytes

The physiologic concentration of electrolytes in serum are approximately the following under normal physiologic conditions: sodium 3105-3358 mg/L; potassium 136.85-207.23 mg/L; chloride 3368.7-3829.7 mg/L; calcium 85-103 mg/L; magnesium 14.59-24.32 mg/L, phosphate 85-150 mg/L, and/or bicarbonate 1281-2013 mg/L. There are noticeable differences between the electrolyte balances found in serum as compared to tears. The greatest difference between tear electrolytes and serum electrolytes is typically found in the levels of potassium. The concentration of potassium is typically much lower in serum (3-5 mmol/L) as compared to tears (20-40 mmol/L).

According to one aspect of the present invention there is provided a method of treating a patient's eye wherein its normal condition has been disrupted or changed. The method of this aspect of the invention is effected by administering a topical ophthalmic formulation comprising physiologic levels of a serum electrolyte in conjunction with an antimicrobial, and anti-inflammatory or steroidal agent. A further aspect of the present invention is wherein the topical ophthalmic formulation comprising physiologic levels of a serum electrolyte comprises potassium in a concentration from about 136.85 to about 207.23 mg/L. A still further aspect of the present invention is wherein the topical ophthalmic formulation comprising physiologic levels of serum electrolytes comprises potassium in a concentration from about 136.85 to about 207.23 mg/L; chloride in a concentration from about 3368.7 to about 3829.68 mg/L; calcium in a concentration from about 85 to about 103 mg/L; magnesium in a concentration from about 14.592 to about 24.32 mg/L; and phosphate in a concentration from about 85 to about 150 mg/L. A yet still further aspect of the present invention is wherein the topical ophthalmic formulation comprising physiologic levels of serum electrolytes comprises sodium in a concentration from about 3105 to about 3358 mg/L; potassium in a concentration from about 136.85 to about 207.23 mg/L; chloride in a concentration from about 3368.7 to about 3829.68 mg/L; calcium in a concentration from about 85 to about 103 mg/L; magnesium in a concentration from about 14.592 to about 24.32 mg/L; phosphate in a concentration from about 85 to about 150 mg/L, and bicarbonate in a concentration from about 1281 to about 2013 mg/L. In addition to the methods of treating an eye wherein its normal condition has been disrupted or changed in a patient, each of the aforementioned formulations or compositions used in these methods are further aspects of the present invention.

Antimicrobial, and Anti-Inflammatory or Steroidal Agents

The topical ophthalmic formulation of the present invention comprises physiologic levels of a serum electrolyte, an antimicrobial agent, and an anti-inflammatory or steroidal agent. The antimicrobial compound of the present invention is selected from, but not limited to the following antimicrobial classes: aminoglycoside, fluoroquinolone, tetralide, or cephalosporin and their ophthalmically-acceptable derivatives. The antimicrobial compound of the present invention is selected from, but not limited to: tobramycin, gentamicin, ciprofloxacin, norfloxacin, ofloxacin, and/or sparfloxacin; or their ophthalmically-acceptable derivatives. The anti-inflammatory compound of the present invention is selected from, but not limited to: diclofenac, bromfenac, dexamethasone and prednisolone. The steroidal compound of the present invention is selected from, but not limited to: prednisolone, dexamethasone, fluorometholone, beta-methasone, and/or corticosterone. For example, ocular steroids are added when indicated in inflammatory conditions of the palpebral and bulbar conjunctiva, cornea and anterior segment of the globe such as allergic conjunctivitis, acne rosacea, superficial punctuate keratitis, herpes zoster keratitis, cyclitis, and where the inherent risk of steroid use in certain infective conjunctivides is accepted to obtain a diminution in edema and inflammation. Ocular steroids are also indicated in surgical trauma, anterior uveitis and corneal injury from chemical, radiation or thermal burns, or penetration of foreign bodies. The antimicrobial agent of the present invention is indicated where the risk of superficial ocular infection is high or where there is an expectation that potentially dangerous numbers of bacteria will be present in the eye.

Conditions/Diseases

According to one aspect of the present invention there is provided a method of treating an ocular disease, injury or disorder in a patient. The method of this aspect of the invention is effected by administering a topical ophthalmically-acceptable formulation comprising therapeutically-effective amounts of antimicrobial, and anti-inflammatory or steroidal agents in combination with physiologic levels of serum electrolytes to a subject in need thereof.

A further aspect of the present invention is wherein said ocular disease, injury or disorder is caused by surgery, physical damage to the eye, glaucoma, macular degeneration, or diabetic retinopathy. A still further aspect of the present invention is wherein the ocular disease, injury or disorder is one caused by vascular leakage in the eye or by inflammation in the eye.

Examples of conditions related to inflammation in the eye include, but are not limited to the following: surgical trauma, dry eye, allergic conjunctivitis, viral conjunctivitis, bacterial conjunctivitis, blepharitis, anterior uveitis, injury from a chemical, radiation or thermal burn, or penetration of a foreign body.

Additional Actives

Unless the intended purpose of use is affected adversely, the ophthalmic formulation of the present invention may further comprise one or more additional therapeutically-active agents. Specific therapeutically-active agents include, but are not limited to: antibacterial antibiotics, synthetic antibacterials, antifungal antibiotics, synthetic antifungals, antineoplastic agents, steroidal anti-inflammatory agents, non-steroidal anti-inflammatory agents, anti-allergic agents, glaucoma-treating agents, antiviral agents, and anti-mycotic agents. Further contemplated are any derivatives of the therapeutically-active agents which may include, but not be limited to: analogs, salts, esters, amines, amides, alcohols and acids derived from an agent of the invention and may be used in place of an agent itself.

Examples of the antibacterial antibiotics include, but are not limited to: aminoglycosides (e.g., amikacin, apramycin, arbekacin, bambermycins, butirosin, dibekacin, dihydrostreptomycin, fortimicin(s), gentamicin, isepamicin, kanamycin, micronomicin, neomycin, neomycin undecylenate, netilmicin, paromomycin, ribostamycin, sisomicin, spectinomycin, streptomycin, tobramycin, trospectomycin), amphenicols (e.g., azidamfenicol, chloramphenicol, florfenicol, thiamphenicol), ansamycins (e.g., rifamide, rifampin, rifamycin sv, rifapentine, rifaximin), β-lactams (e.g., carbacephems (e.g., loracarbef), carbapenems (e.g., biapenem, imipenem, meropenem, panipenem), cephalosporins (e.g., cefaclor, cefadroxil, cefamandole, cefatrizine, cefazedone, cefazolin, cefcapene pivoxil, cefclidin, cefdinir, cefditoren, cefepime, cefetamet, cefixime, cefmenoxime, cefodizime, cefonicid, cefoperazone, cefforanide, cefotaxime, cefotiam, cefozopran, cefpimizole, cefpiramide, cefpirome, cefpodoxime proxetil, cefprozil, cefroxadine, cefsulodin, ceftazidime, cefteram, ceftezole, ceftibuten, ceftizoxime, ceftriaxone, cefuroxime, cefuzonam, cephacetrile sodium, cephalexin, cephaloglycin, cephaloridine, cephalosporin, cephalothin, cephapirin sodium, cephradine, pivcefalexin), cephamycins (e.g., cefbuperazone, cefmetazole, cefminox, cefotetan, cefoxitin), monobactams (e.g., aztreonam, carumonam, tigemonam), oxacephems, flomoxef, moxalactam), penicillins (e.g., amdinocillin, amdinocillin pivoxil, amoxicillin, ampicillin, apalcillin, aspoxicillin, azidocillin, azlocillin, bacampicillin, benzylpenicillinic acid, benzylpenicillin sodium, carbenicillin, carindacillin, clometocillin, cloxacillin, cyclacillin, dicloxacillin, epicillin, fenbenicillin, floxacillin, hetacillin, lenampicillin, metampicillin, methicillin sodium, mezlocillin, nafcillin sodium, oxacillin, penamecillin, penethamate hydriodide, penicillin g benethamine, penicillin g benzathine, penicillin g benzhydrylamine, penicillin g calcium, penicillin g hydrabamine, penicillin g potassium, penicillin g procaine, penicillin n, penicillin o, penicillin v, penicillin v benzathine, penicillin v hydrabamine, penimepicycline, phenethicillin potassium, piperacillin, pivampicillin, propicillin, quinacillin, sulbenicillin, sultamicillin, talampicillin, temocillin, ticarcillin), other (e.g., ritipenem), lincosamides (e.g., clindamycin, lincomycin), macrolides (e.g., azithromycin, carbomycin, clarithromycin, dirithromycin, erythromycin, erythromycin acistrate, erythromycin estolate, erythromycin glucoheptonate, erythromycin lactobionate, erythromycin propionate, erythromycin stearate, josamycin, leucomycins, midecamycins, miokamycin, oleandomycin, primycin, rokitamycin, rosaramicin, roxithromycin, spiramycin, troleandomycin), polypeptides (e.g., amphomycin, bacitracin, capreomycin, colistin, enduracidin, enviomycin, fusafungine, gramicidin s, gramicidin(s), mikamycin, polymyxin, pristinamycin, ristocetin, teicoplanin, thiostrepton, tuberactinomycin, tyrocidine, tyrothricin, vancomycin, viomycin, virginiamycin, zinc bacitracin), tetracyclines (e.g., apicycline, chlortetracycline, clomocycline, demeclocycline, doxycycline, guamecycline, lymecycline, meclocycline, methacycline, minocycline, oxytetracycline, penimepicycline, pipacycline, rolitetracycline, sancycline, tetracycline), and others (e.g., cycloserine, mupirocin, tuberin).

Examples of the synthetic antibacterials include, but are not limited to: 2,4-diaminopyrimidines (e.g., brodimoprim, tetroxoprim, trimethoprim), nitrofurans (e.g., furaltadone, furazolium chloride, nifuradene, nifuratel, nifurfoline, nifurpirinol, nifurprazine, nifurtoinol, nitrofurantoin), quinolones and analogs (e.g., cinoxacin, ciprofloxacin, clinafloxacin, difloxacin, enoxacin, fleroxacin, flumequine, grepafloxacin, lomefloxacin, miloxacin, nadifloxacin, nalidixic acid, norfloxacin, ofloxacin, oxolinic acid, pazufloxacin, pefloxacin, pipemidic acid, piromidic acid, rosoxacin, rufloxacin, sparfloxacin, temafloxacin, tosufloxacin, trovafloxacin), sulfonamides (e.g., acetyl sulfamethoxypyrazine, benzylsulfamide, chloramine-b, chloramine-t, dichloramine t, $n^2$-formylsulfisomidine, $n^4$-β-d-glucosylsulfanilamide, mafenide, 4'-(methylsulfamoyl)sulfanilanilide, noprylsulfamide, phthalylsulfacetamide, phthalylsulfathiazole, salazosulfadimidine, succinylsulfathiazole, sulfabenzamide, sulfacetamide, sulfachlorpyridazine, sulfachrysoidine, sulfacytine, sulfadiazine, sulfadicramide, sulfadimethoxine, sulfadoxine, sulfaethidole, sulfaguanidine, sulfaguanol, sulfalene, sulfaloxic acid, sulfamerazine, sulfameter, sulfamethazine, sulfamethizole, sulfamethomidine, sulfamethoxazole, sulfamethoxypyridazine, sulfametrole, sulfamidocchrysoidine, sulfamoxole, sulfanilamide, 4-sulfanilamidosalicylic acid, n⁴-sulfanilylsulfanilamide, sulfanilylurea, n-sulfanilyl-3,4-xylamide, sulfanitran, sulfaperine, sulfaphenazole, sulfaproxyline, sulfapyrazine, sulfapyridine, sulfasomizole, sulfasymazine, sulfathiazole, sulfathiourea, sulfatolamide, sulfisomidine, sulfisoxazole) sulfones (e.g., acedapsone, acediasulfone, acetosulfone sodium, dapsone, diathymosulfone, glucosulfone sodium, solasulfone, succisulfone, sulfanilic acid, p-sulfanilylbenzylamine, sulfoxone sodium, thiazolsulfone), and others (e.g., clofoctol, hexedine, methenamine, methenamine anhydromethylene-citrate, methenamine hippurate, methenamine mandelate, methenamine sulfosalicylate, nitroxoline, taurolidine, xibornol).

Examples of the antifungal antibiotics include, but are not limited to: polyenes (e.g., amphotericin b, candicidin, dennostatin, filipin, fungichromin, hachimycin, hamycin, lucensomycin, mepartricin, natamycin, nystatin, pecilocin, perimycin), others (e.g., azaserine, griseofulvin, oligomycins, neomycin undecylenate, pyrrolnitrin, siccanin, tubercidin, viridin).

Examples of the synthetic antifungals include, but are not limited to: allylamines (e.g., butenafine, naftifine, terbinafine), imidazoles (e.g., bifonazole, butoconazole, chlordantoin, chlormiidazole, clotrimazole, econazole, enilconazole, fenticonazole, flutrimazole, isoconazole, ketoconazole, lanoconazole, miconazole, omoconazole, oxiconazole nitrate, sertaconazole, sulconazole, tioconazole), thiocarbamates (e.g., tolciclate, tolindate, tolnaftate), triazoles (e.g., fluconazole, itraconazole, saperconazole, terconazole) others (e.g., acrisorcin, amorolfine, biphenamine, bromosalicylchloranilide, buclosamide, calcium propionate, chlorphenesin, ciclopirox, cloxyquin, coparaffinate, diamthazole dihydrochloride, exalamide, flucytosine, halethazole, hexetidine, loflucarban, nifuratel, potassium iodide, propionic acid, pyrithione, salicylanilide, sodium propionate, sulbentine, tenonitrozole, triacetin, ujothion, undecylenic acid, zinc propionate).

Examples of the antineoplastic agents include, but are not limited to: antineoplastc antibiotics and analogs (e.g., aclacinomycins, actinomycin anthramycin, azaserine, bleomycins, cactinomycin, carubicin, carzinophilin, chromomycins, dactinomycin, daunorubicin, 6-diazo-5-oxo-L-norleucine, doxorubicin, epirubicin, idarubicin, menogaril, mitomycins, mycophenolic acid, nogalamycin, olivomycines, peplomycin, pirarubicin, plicamycin, porfiromycin, puromycin, streptonigrin, streptozocin, tubercidin, zinostatin, zorubicin), anti-metabolites exemplified by folic acid analogs (e.g., denopterin, edatrexate, methotrexate, piritrexim, pteropterin, TOMUDEX®, trimetrexate), purine analogs (e.g., cladribine, fludarabine, 6-mercaptopurine, thiamiprine, thioguanine), pyrimidine analogs (e.g., ancitabine, azacitidine, 6-azauridine, carmofur, cytarabine, doxifluridine, emitefur, enocitabine, floxuridine, fluorouracil, gemcitabine, tagafur).

Examples of the steroidal anti-inflammatory agents include, but are not limited to: 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, and triamcinolone hexacetonide.

Examples of the non-steroidal anti-inflammatory agents include, but are not limited to: aminoarylcarboxylic acid derivatives (e.g., enfenamic acid, etofenamate, flufenamic acid, isonixin, meclofenamic acid, mefenamic acid, niflumic acid, talniflumate, terofenamate, tolfenamic acid), arylacetic acid derivatives (e.g., aceclofenac, acemetacin, alclofenac, amfenac, amtolmetin guacil, bromfenac, bufexamac, cinmetacin, clopirac, diclofenac sodium, etodolac, felbinac, fenclozic acid, fentiazac, glucametacin, ibufenac, indomethacin, isofezolac, isoxepac, lonazolac, metiazinic acid, mofezolac, oxametacine, pirazolac, proglumetacin, sulindac, tiaramide, tolmetin, tropesin, zomepirac), arylbutyric acid derivatives (e.g., bumadizon, butibufen, fenbufen, xenbucin), arylcarboxylic acids (e.g., clidanac, ketorolac, tinoridine), arylpropionic acid derivatives (e.g., alminoprofen, benoxaprofen, bermoprofen, bucloxic acid, carprofen, fenoprofen, flunoxaprofen, flurbiprofen, ibuprofen, ibuproxam, indoprofen, ketoprofen, loxoprofen, naproxen, oxaprozin, piketoprolen, pirprofen, pranoprofen, protizinic acid, suprofen, tiaprofenic acid, ximoprofen, zaltoprofen), pyrazoles (e.g., difenamizole, epirizole), pyrazolones (e.g., apazone, benzpiperylon, feprazone, mofebutazone, morazone, oxyphenbutazone, phenylbutazone, pipebuzone, propyphenazone, ramifenazone, suxibuzone, thiazolinobutazone), salicylic acid derivatives (erg., acetaminosalol, aspirin, benorylate, bromosaligenin, calcium acetylsalicylate, diflunisal, etersalate, fendosal, gentisic acid, glycol salicylate, imidazole salicylate, lysine acetylsalicylate, mesalamine, morpholine salicylate, 1-naphthyl salicylate, olsalazine, parsalmide, phenyl acetylsalicylate, phenyl salicylate, salacetamide, salicylamide o-acetic acid, salicylsulfuric acid, salsalate, sulfasalazine), thiazinecarboxamides (e.g., am piroxicam, droxicam, isoxicam, lornoxicam, piroxicam, tenoxicam), E-acetamidocaproic acid, s-adenosylmethionine, 3-amino-4-hydroxybutyric acid, amixetrine, bendazac, benzydamine, α-bisabolol, bucolome, difenpiramide, ditazol, emorfazone, fepradinol, guaiazulene, nabumetone, nimesulide, oxaceprol, paranyline, perisoxal, proquazone, superoxide dismutase, tenidap, and zileuton.

Examples of anti-allergic agents include, but are not limited to: tranilast, ketotifen fumarate, pheniramine, diphenhydramine hydrochloride, and sodium cromoglicate.

Examples of glaucoma-treating agents include, but are not limited to: pilocarpine hydrochloride, latanoprost, timolol, and isopropylunoprostone.

Examples of antiviral agents include, but are not limited to: idoxuridine, acyclovir, and trifluorouridine.

Examples of anti-mycotic agents include, but are not limited to: pimaricin, fluconazole, miconazole, amphotericin B, flucytosine, and itraconazole.

Methods

According to one aspect of the present invention there is provided a method of treating a patient's eye wherein its normal condition has been disrupted or changed. The method of this aspect of the invention is effected by administering a topical ophthalmically-acceptable formulation comprising physiologic levels of serum electrolytes in combination with a therapeutically-effective amount of an ophthalmically-active antimicrobial, and an ophthalmically-active anti-inflammatory or steroidal agent to treat an ocular disease, injury or disorder. A further aspect of the present invention is wherein the topical ophthalmically-acceptable formulation comprising physiologic levels of serum electrolytes in combination with a therapeutically-effective amount of an ophthalmically-active antimicrobial, and an ophthalmically-active anti-inflammatory or steroidal agent to treat an ocular disease, injury or disorder comprises potassium in a concentration from about 136.85 to about 207.23 mg/L. A still further aspect of the present invention is wherein the topical ophthalmically-acceptable formulation comprising physiologic levels of serum electrolytes in combination with a therapeutically-effective amount of an ophthalmically-active antimicrobial, and an ophthalmically-active anti-inflammatory or steroidal agent to treat an ocular disease, injury or disorder comprises: potassium in a concentration from about 136.85 to about 207.23 mg/L; chloride in a concentration from about 3368.7 to about 3829.68 mg/L; calcium in a concentration from about 85 to about 103 mg/L; magnesium in a concentration from about 14.592 to about 24.32 mg/L; and phosphate in a concentration from about 85 to about 150 mg/L. A yet still further aspect of the present invention is wherein the topical ophthalmically-acceptable formulation comprising physiologic levels of serum electrolytes in combination with a therapeutically-effective amount of an ophthalmically-active antimicrobial, and an ophthalmically-active anti-inflammatory or steroidal agent to treat an ocular disease, injury or disorder comprises: sodium in a concentration from about 3105 to about 3358 mg/L; potassium in a concentration from about 136.85 to about 207.23 mg/L; chloride in a concentration from about 3368.7 to about 3829.68 mg/L; calcium in a concentration from about 85 to about 103 mg/L; magnesium in a concentration from about 14.592 to about 24.32 mg/L; phosphate in a concentration from about 85 to about 150 mg/L, and bicarbonate in a concentration from about 1281 to about 2013 mg/L.

Viscosity/Osmolality/pH

The ophthalmic formulation when in an aqueous or non-aqueous form may also contain, but not be limited to: suspending agents (e.g., polyvinyl pyrrolidone, glycerin monostearate, sorbitan esters, lanolin alcohols) and dispersing agents (e.g., surfactants such as tyloxapol and polysorbate 80, ionic polymers such as sodium alginate) in addition to the agents listed above, to ensure that the ophthalmic formulation is satisfactorily dispersed in a uniform microparticulate suspension.

When the ophthalmic formulation is in the form of an aqueous suspension or solution, a non-aqueous suspension or solution, or a gel or ointment it is preferable to use a pH modifier to make the formulation have a pH between about 4 and 8, more preferably between about 6.8 to about 7.5. A preferred pH modifier is hydrochloric acid, sulfuric acid, boric acid, sodium hydroxide or any other ophthalmically-acceptable pH modifier.

According to a further aspect of the present invention a topical ophthalmically-acceptable formulation comprising physiologic levels of serum electrolytes in combination with a therapeutically-effective amount of an ophthalmically-active antimicrobial and an ophthalmically-active anti-inflammatory or steroidal agent to treat an ocular disease, injury or disorder may further comprise an ophthalmically-acceptable excipient which modulates the osmolality of the formulation from about 200 to about 500 mOsm/Kg, preferably from about 250 to about 400 mOsm/Kg, and more preferably from about 280 to about 320 mOsm/Kg. Examples of osmolality excipients include, but are not limited to: dextrose, sodium chloride, potassium chloride, glycerin, various buffers and the like.

Sugars

It is further contemplated by the present invention that a topical ophthalmically-acceptable formulation comprising physiologic levels of serum electrolytes in combination with a therapeutically-effective amount of an ophthalmically-active antimicrobial, and an ophthalmically-active anti-inflammatory or steroidal agent to treat an ocular disease, injury or disorder may further comprise from about 10 to about 1500 mg/L, and more preferred from about 700 to about 1250 mg/L of a nutrient sugar. In yet a further contemplation of the present invention the nutrient sugar of the formulation is a monosaccharide, oligosaccharide or polysaccharide. Examples of the nutrient sugars include, but are not limited to: dextrose, fructose, galactose, glucose, mannose, N-acetyl-galactosamine, N-acetyl-glucosamine, N-acetyl-neuraminic acid, and xylose. In yet still a further contemplation of the invention provides that the nutrient sugar of the present formulation is dextrose at a concentration from about 700 to about 1250 mg/L.

Excipients

The formulation may contain various excipients incorporated ordinarily, such as buffering agents (e.g., phosphate buffers, borate buffers, citrate buffers, tartarate buffers, acetate buffers, amino acids, sodium acetate, sodium citrate and the like), isotonicity agents (e.g., saccharides such as sorbitol, glucose and mannitol, polyhydric alcohols such as glycerin, concentrated glycerin, polyethylene glycol and propylene glycol, salts such as sodium chloride), preservatives or antiseptics (e.g., benzalkonium chloride, benzethonium chloride, p-oxybenzoates such as methyl p-oxybenzoate or ethyl p-oxybenzoate, benzyl alcohol, phenethyl alcohol, sorbic acid or its salt, thimerosal, chlorobutanol, other quaternary amines and the like), solubilizing aids or stabilizing agents (e.g., cyclodextrins and their derivatives, water-soluble polymers such as polyvinyl pyrrolidone, or carbomer, surfactants such as polysorbate 80 (Tween 80)), pH modifiers (e.g., hydrochloric acid, acetic acid, phosphoric acid, sodium hydroxide, potassium hydroxide, ammonium hydroxide and the like), thickening agents (e.g., hydroxyethyl cellulose, hydroxypropyl cellulose, methyl cellulose, hydroxypropylmethyl cellulose, carboxymethyl cellulose and their salts), chelating agents (e.g., sodium edetate, sodium citrate, condensed sodium phosphate) and the like. Descriptions of compounds used in standard ophthalmic formulations may be found in, for example, Remington's Pharmaceutical Sciences, latest edition, Mack Publishing Co. Easton Pa.

Non-limiting examples of the contemplated excipients include a buffer, osmotic agent, demulcent, surfactant, emollient, tonicity agent, and/or a preservative component.

Preparations

The formulation for ophthalmic conditions according to the present invention can be mixed with a ophthalmically acceptable carrier, excipient or diluent and formulated by a known method into a composition or formulation in various dosage forms such as injection solutions, eye drops and ophthalmic gels or ointments, and it is especially preferred to be used in a topical dosage form, preferably an eye drop formulation in solution or suspension form or an ophthalmic gel or ointment.

The ophthalmic formulation may for example be aqueous formulations such as aqueous eye drops, aqueous suspension eye drops, viscous eye drops and solubilized eye drops as well as non-aqueous formulations such as non-aqueous eye drops and non-aqueous suspension eye drops, or an ophthalmic gel or ointment.

The eye drop formulation in the form of an aqueous suspension preferably contains sodium citrate as a buffering agent, glycerin and/or propylene glycol as an isotonicity agent and polyvinyl pyrrolidone as a suspending agent.

The ophthalmic ointment may employ an ointment base known per se, such as purified lanolin, petrolatum, plastibase, liquid paraffin, polyethylene glycol and the like.

In another aspect of this invention, the ophthalmic formulation may be incorporated in a carrier system, which may be water, gel or ointment base. In still another aspect of this invention, said carrier system is a clear and stable pharmaceutical preparation, suitable for ocular treatment.

Kits

The present invention also provides for an ophthalmic kit comprising a composition for use in a topical ophthalmic formulation comprising a topical ophthalmically-acceptable formulation comprising a therapeutically-effective amount of an ophthalmically-active antimicrobial, and an ophthalmically-active anti-inflammatory or steroidal agent in combination with physiologic levels of serum electrolytes and a means to apply the composition to the eye. The ophthalmic kits may contain an application means which is an eye dropper, an eye cup, an eye spray or gel ointment tube and can comprise a single dose or a multi dose of the composition or formulation in a single container.

Administration

The ophthalmic composition or formulation of the present invention may be administered to a patient which is or may be suffering from an ophthalmic injury, disease or disorder (e.g., human, rat, mouse, rabbit, dog, cat, cattle, horse, monkey). The ophthalmic composition or formulation of the present invention also can be administered to a patient following ophthalmic surgery. The composition or formulation is given in an amount sufficient to cure, treat, or at least partially arrest the symptoms or complications of the surgery, injury, disease or disorder. Amounts effective for this use will depend on the severity and course of the surgery, injury, disease or disorder, the patient's health status and response to the composition or formulation, and the judgment of the treating physician.

The formulation of the present invention and its subsequent administration is within the skill of those in the art. Dosing is dependent on severity and responsiveness of the disease state to be treated, with the course of treatment lasting from one day to several months, or until a cure is effected or a diminution of the disease state is achieved. Optimal dosing schedules can be calculated from measurements of drug accumulation in the body of the patient.

EXAMPLES

Having now generally described the invention, the same will be more readily understood through reference to the following examples which are provided by way of illustration, and are not intended to be limiting of the present invention, unless specified.

Example 1

Electrolyte Component:

| | |
|---|---|
| Electrolyte 1—Sodium | about 3200 mg/L; |
| Electrolyte 2—Potassium | about 160 mg/L; |
| Electrolyte 3—Chloride | about 3500 mg/L; |
| Electrolyte 4—Calcium | about 95 mg/L; |
| Electrolyte 5—Magnesium | about 20 mg/L; |
| Electrolyte 6—Phosphate | about 120 mg/L; and |
| Electrolyte 7—Bicarbonate | about 1650 mg/L |

Antibiotic Component:

| | |
|---|---|
| Tobramycin | about 0.30% |

Anti-Inflammatory Component:

| | |
|---|---|
| Prednisolone Acetate | about 1% |

Other Ingredients:

| | |
|---|---|
| Hydroxypropyl methylcellulose E4M | about 0.3% |
| Polysorbate 80 | about 0.05% |
| Benzalkonium Chloride | about 0.005% |
| 1N Sodium Hydroxide | about 0.05 mL |
| Citric Acid | about 0.25% |
| Boric Acid | about 0.30% |
| pH | about 7.2 |
| osmolality (mOsm/kg) | about 290 |

Example 2

Electrolyte Component:

| | |
|---|---|
| Potassium | about 160 mg/L; |

Anti-Inflammatory Component:

| | |
|---|---|
| Prednisolone Acetate | about 1% |

Antibiotic Component:

| | |
|---|---|
| Tobramycin | about 0.30% |

Other Ingredients:

| | |
|---|---|
| Hydroxypropyl methylcellulose E4M | about 0.3% |
| Polysorbate 80 | about 0.05% |
| Benzalkonium Chloride | about 0.005% |
| 1N Sodium Hydroxide | about 0.05 mL |
| Citric Acid | about 0.25% |
| Boric Acid | about 0.30% |
| pH | about 7.2 |
| osmolality (mOsm/kg) | about 290 |

Example 3

Electrolyte Component:

| | |
|---|---|
| Potassium | about 160 mg/L; |

Antibiotic Component:

| | |
|---|---|
| Gentamicin | about 0.30% |

Anti-Inflammatory Component:

| | |
|---|---|
| Dexamethasone | about 1% |

-continued

| Other Ingredients: | |
|---|---|
| Hydroxypropyl methylcellulose E4M | about 0.3% |
| Polysorbate 80 | about 0.05% |
| Benzalkonium Chloride | about 0.005% |
| 1N Sodium Hydroxide | about 0.05 mL |
| Citric Acid | about 0.25% |
| Boric Acid | about 0.30% |
| pH | about 7.2 |
| osmolality (mOsm/kg) | about 290 |

Example 4

Electrolyte Component:

| Electrolyte 1—Sodium | about 3200 mg/L; |
|---|---|
| Electrolyte 2—Potassium | about 160 mg/L; |
| Electrolyte 3—Chloride | about 3500 mg/L; |
| Electrolyte 4—Calcium | about 95 mg/L; |
| Electrolyte 5—Magnesium | about 20 mg/L; |
| Electrolyte 6—Phosphate | about 120 mg/L; and |
| Electrolyte 7—Bicarbonate | about 1650 mg/L |

Antibiotic Component:

| Tobramycin | about 0.30% |
|---|---|

Anti-Inflammatory Component:

| Dexamethasone | about 1% |
|---|---|

Other Ingredients:

| Hydroxypropyl methylcellulose E4M | about 0.3% |
|---|---|
| Polysorbate 80 | about 0.05% |
| Benzalkonium Chloride | about 0.005% |
| 1N Sodium Hydroxide | about 0.05 mL |
| Citric Acid | about 0.25% |
| Boric Acid | about 0.30% |
| pH | about 7.2 |
| osmolality (mOsm/kg) | about 290 |

Example 5

A composition formulated for topical ophthalmic administration contained physiologic levels of serum electrolytes, an antimicrobial compound, an anti-inflammatory or steroidal compound, and benzalkonium chloride as a preservative. In one embodiment, the composition contained 150 ppm to 250 ppm benzalkonium chloride. In one embodiment, the composition contained 175 ppm to 225 ppm benzalkonium chloride. In one embodiment, the composition contained 200 ppm benzalkonium chloride. In one embodiment, the composition was formulated as follows:

A composition formulated for topical ophthalmic administration contained physiologic levels of serum electrolytes, an antimicrobial compound, an anti-inflammatory or steroidal compound, and benzalkonium chloride as a preservative. In one embodiment, the composition contained 150 ppm to 250 ppm benzalkonium chloride. In one embodiment, the composition contained 175 ppm to 225 ppm benzalkonium chloride. In one embodiment, the composition contained 200 ppm benzalkonium chloride. In one embodiment, the composition was formulated as follows:

| Components | Function | Amount/mL | % |
|---|---|---|---|
| Prednisolone Acetate USP | Active Ingredient | 0.0104 g (0.01 g/mL label claim) | 1.040 |
| Tobramycin USP | Active | 0.00303 g (0.003 g/mL label claim) | 0.303 |
| Hydroxypropyl Methylcellulose USP | Suspending and wetting agent | 0.003 g | 0.300 |
| Polysorbate 80 NF | Wetting agent | 0.0005 g | 0.0500 |
| Potassium Chloride USP | Tonicity | 0.000275 g | 0.0275 |
| Calcium Chloride, Dihydrate USP | Tonicity | 0.000315 g | 0.0315 |
| Magnesium Chloride, Hexahydrate USP | Tonicity | 0.000125 g | 0.0125 |
| Sodium Phosphate Dibasic, Anhydrous USP | Buffering Agent | 0.00015 g | 0.015 |
| Benzalkonium Chloride NF, 50% Solution | Preservative | 0.000405 (0.0002025 g of 100% BAK | 0.02025 (as 100% BAK) |
| Sodium Chloride USP | Tonicity | 0.00505 g | 0.505 |
| Sodium Borate Decahydrate USP | Buffering Agent | 0.0045 g | 0.450 |
| Sodium Sulfate Decahydrate USP | Tonicity | 0.0038 g | 0.380 |
| Sulfuric Acid | pH adjustment | As required for pH 6.85 | As required for pH 6.85 |
| Water For Injection USP | Solvent | q.s. to 1 mL | q.s. to 100% |

The formulations in Example 5 containing benzalkonium chloride within the pharmaceutically acceptable range of 200 ppm (i.e., ±10 and ±15%), were effective against a broad range of microorganisms. Efficacy was demonstrated by inoculating high concentrations of each of 26 different types of bacteria or fungi with the formulation of Example 5, then measuring the recovered population after 60 minutes of exposure. The results are shown in the table below:

| Organism | ATCC[1] Number | $Log_{10}$ Reduction in Microbial Count After 60 Minutes Exposure |
|---|---|---|
| Staphylococcus aureus | 6538 | ≥5.88 |
| Klebsiella pneumoniae | 13883 | ≥5.28 |
| Enterobacter aerogenes | 13048 | ≥5.70 |
| Streptococcus pneumoniae | 33400 | ≥4.66 |
| Acinetobacter calcoaceticus | 23055 | ≥5.26 |
| Proteus hauseri | 13315 | ≥5.54 |
| Haemophilus influenzae | 33391 | ≥5.89 |
| Neisseria elongate | 25295 | ≥5.41 |
| Staphylococcus epidermidis | 12228 | ≥5.76 |
| Streptococcus pyogenes | 49399 | ≥5.75 |
| Streptococcus mutans | 25175 | ≥5.41 |
| Escherichia coli | 8739 | ≥5.70 |
| Haemophilus aegyptius | 11116 | ≥5.82 |
| Neisseria cinerea | 14685 | ≥5.41 |
| Candida albicans | 10231 | ≥5.75 |
| Staphylococcus epidermidis | 700579 | ≥5.43 |
| Staphylococcus epidermidis | 700566 | ≥5.50 |
| Pseudomonas aeruginosa | 9027 | ≥5.52 |
| Staphylococcus aureus | 13301 | ≥5.63 |
| Staphylococcus aureus | 11632 | ≥5.68 |
| Proteus mirabilis | 29906 | ≥5.57 |
| Morganella morganii | 25830 | ≥5.61 |
| Moraxella lacunata | 17970 | ≥6.10 |
| Aspergillus brasiliensis | 16404 | ≥5.56 |
| Staphylococcus aureus | 700699 | ≥5.72 |
| Streptococcus pneumoniae | 700671 | ≥5.21 |

[1]American Type Culture Collection

As shown in the table above, all 26 microorganisms were killed quickly, with $\log_{10}$ reductions in population ranging from ≥4.66 logs to ≥6.10 logs. The formulations did not interfere with the efficacy of the antibiotic component.

The formulations in Example 5 were stable after 24-month storage at 25° C. Data from assessing various parameters are shown in the following table.

| Test | Result after 24 months storage |
|---|---|
| Prednisolone acetate concentration | 102% of theoretical amount added (no change) |
| Tobramycin concentration | 93.2% of theoretical amount added (7% change) |
| pH | 97% of starting value (3% change) |
| Benzalkonium Chloride concentration | 101.4% of theoretical amount added (no change) |
| Antimicrobial Effectiveness Test (USP <51>) | Pass (USP <51> criteria met) |

In addition to demonstrating stability of the Example 5 formulation, the data demonstrated efficacy of the 0.02% benzalkonium chloride preservative following shelf-life storage.

A further non-limiting example of a tobramycin and prednisolone electrolyte formulation with ranges is provided below:

Prednisolone Acetate about 0.9 to about 1.1%/Tobramycin about 0.2 to about 0.4% Ophthalmic Suspension Quantitative Composition

| Raw Materials | Pharmaceutical Grade | mg/mL |
|---|---|---|
| Prednisolone Acetate | USP | About 9 to About 11 |
| Tobramycin | USP | About 2 to About 4 |
| Hydroxypropyl methylcellulose E4M | USP | About 2 to About 4 |
| Polysorbate 80 | NF | About 0.4 to About 0.6 |
| Potassium Chloride | USP | About 0.25 to About 0.3 |
| Calcium Chloride Dihydrate | USP | About 0.28 to About 0.35 |
| Magnesium Chloride Hexahydrate | USP | About 0.1 to About 0.15 |
| Sodium Phosphate Dibasic, Anhydrous | USP | About 0.1 to About 0.2 |
| Benzalkonium Chloride | NF | About 0.05 to About 0.055 |
| Sodium Chloride | USP | About 4 to About 6 |
| Sodium Borate Decahydrate | NF | About 4 to About 5 |
| Sodium Sulfate Decahydrate | USP | About 3.5 to About 4.0 |
| Sulfuric Acid | NF | To adjust pH |
| Purified Water | USP | Q.S. to volume |

A further non-limiting example of a prepared tobramycin and prednisolone electrolyte formulation is provided below:
Prednisolone Acetate 1.0%/Tobramycin 0.3% Ophthalmic Suspension Quantitative Composition

| Raw Materials | Pharmaceutical Grade | mg/mL |
|---|---|---|
| Prednisolone Acetate | USP | 10.000 |
| Tobramycin | USP | 3.0000 |
| Hydroxypropyl methylcellulose E4M | USP | 3.0000 |
| Polysorbate 80 | NF | 0.5000 |
| Potassium Chloride | USP | 0.2750 |
| Calcium Chloride Dihydrate | USP | 0.3150 |
| Magnesium Chloride Hexahydrate | USP | 0.1250 |
| Sodium Phosphate Dibasic, Anhydrous | USP | 0.1500 |
| Benzalkonium Chloride | NF | 0.0525 |
| Sodium Chloride | USP | 5.0500 |
| Sodium Borate Decahydrate | NF | 4.5000 |
| Sodium Sulfate Decahydrate | USP | 3.8000 |
| Sulfuric Acid | NF | To adjust pH |
| Purified Water | USP | Q.S. to volume |

A non-limiting example of the manufacturing preparation for the above tobramycin and prednisolone electrolyte formulation is provided below:

1. Reduce the particle size of the prednisolone acetate to the specified size range;
2. Sterilize the prednisolone acetate;
3. Combine, mix and then sterilize the tobramycin and the excipient ingredients;
4. Aseptically combine and mix the sterile predisolone acetate with the sterile mixture of the tobramycin and the other ingredients; and
5. Aseptically fill the final suspension into the container/closure system.

The release specifications for the above prepared tobramycin and prednisolone electrolyte formulation are provided below:

Finished Drug Product Specifications

| Test | Test Methods | Specifications |
|---|---|---|
| Appearance | USP | Off white to slightly straw yellow suspension |
| pH | USP <791> | About 5 to About 8 |
| Osmolality | USP <785> | About 250 to About 400 mOsm/Kg |
| Prednisolone Acetate Assay | *TM-00158 | About 8 to About 12 mg/mL |
| Tobramycin Assay | *TM-00160 | About 2 to about 4 mg/mL |
| Benzalkonium Chloride Assay | *TM-00161 | About 0.04 to about 0.06 mg/mL |
| Predisolone Acetate Particle Size Distribution | *TM-00166 | a. < or = About 4 µm: About 95% to 99.0% by volume. b. < or = About 6 µm: About 99% to 99.9% by volume |
| Sterility | **TM 200508204-01 | No growth within About 14 days |

All references cited herein, including patents, patent applications, and publications, are hereby incorporated by reference in their entireties, whether previously specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A topical ophthalmic formulation comprising:
   (a) physiologic levels of electrolytes mimicking serum levels;
   (b) an antimicrobial compound;
   (c) an anti-inflammatory or steroidal compound, and
   (d) 150 ppm to 250 ppm benzalkonium chloride as a preservative,
   the formulation excluding serum.

2. The formulation of claim 1 wherein (a), (b), (c), and (d) are in a single topical ophthalmic formulation.

3. The formulation of claim 1 wherein the antimicrobial compound is an aminoglycoside, fluoroquinolone, tetralide, and/or cephalosporin or their ophthalmically-acceptable derivatives.

4. The formulation of claim 1 wherein the antimicrobial compound is tobramycin, gentamicin, ciproflaxacin, norfloxacin, ofloxacin, and/or sparfloxacin; or their ophthalmically-acceptable derivatives.

5. The formulation of claim 1 wherein the antimicrobial compound is tobramycin or its ophthalmically-acceptable derivatives.

6. The formulation of claim 1 wherein the anti-inflammatory compound is diclofenac, bromfenac, dexamethasone and/or prednisolone or their ophthalmically-acceptable derivatives.

7. The formulation of claim 1 wherein the anti-inflammatory compound is prednisolone or its ophthalmically-acceptable derivatives.

8. The formulation of claim 1 wherein the steroidal compound is prednisolone, dexamethasone, fluormetholone, beta-methasone, and/or corticosterone or their ophthalmically-acceptable derivatives.

9. The formulation of claim 1 wherein the steroidal compound is prednisolone or its ophthalmically-acceptable derivatives.

10. The formulation of claim 1 which comprises potassium in a concentration from about 136.85 to about 207.23 mg/L.

11. The formulation of claim 1 which comprises the following ranges of electrolytes:
   potassium in a concentration from about 136.85 to about 207.23 mg/L;
   chloride in a concentration from about 3368.7 to about 3829.68 mg/L;
   calcium in a concentration from about 85 to about 103 mg/L;
   magnesium in a concentration from about 14.592 to about 24.32 mg/L; and
   phosphate in a concentration from about 85 to about 150 mg/L.

12. The formulation of claim 1 which comprises the following ranges of electrolytes:
   sodium in a concentration from about 3105 to about 3358 mg/L;
   potassium in a concentration from about 136.85 to about 207.23 mg/L;
   chloride in a concentration from about 3368.7 to about 3829.68 mg/L;
   calcium in a concentration from about 85 to about 103 mg/L;
   magnesium in a concentration from about 14.592 to about 24.32 mg/L;
   phosphate in a concentration from about 85 to about 150 mg/L; and
   bicarbonate in a concentration from about 1281 to about 2013 mg/L.

13. The formulation of claim 1 further comprising an additional ophthalmically-acceptable excipient.

14. The formulation of claim 13 wherein the excipient is a buffer, osmotic agent, demulcent, surfactant, emollient, and/or tonicity agent.

15. The formulation of claim 14 wherein the osmolality of the formulation is from about 200 to about 500 mOsm/Kg.

16. The formulation of claim 14 wherein the osmolality of the formulation is from about 250 to about 400 mOsm/Kg.

17. The formulation of claim 1 wherein the formulation is an aqueous, non-aqueous, gel, or ointment formulation.

18. The formulation of claim 1 containing 175 ppm to 225 ppm benzalkonium chloride as a preservative.

19. The formulation of claim 1 containing 200 ppm benzalkonium chloride as a preservative.

20. A composition for use in a topical ophthalmic formulation comprising:

| Component | Amount/mL | % |
|---|---|---|
| Prednisolone Acetate USP | 0.01 g | 1.040 |
| Tobramycin USP | 0.003 g | 0.303 |
| Hydroxypropyl Methylcellulose USP | 0.003 g | 0.300 |
| Polysorbate 80 NF | 0.0005 g | 0.0500 |
| Potassium Chloride USP | 0.000275 g | 0.0275 |
| Calcium Chloride, Dihydrate USP | 0.000315 g | 0.0315 |
| Magnesium Chloride, Hexahydrate USP | 0.000125 g | 0.0125 |
| Sodium Phosphate Dibasic, Anhydrous USP | 0.00015 g | 0.015 |
| Benzalkonium Chloride NF, 50% Solution | 0.000405 (0.0002025 g of 100% BAK) | 0.02025 (as 100% BAK) |
| Sodium Chloride USP | 0.00505 g | 0.505 |
| Sodium Borate Decahydrate USP | 0.0045 g | 0.450 |
| Sodium Sulfate Decahydrate USP | 0.0038 g | 0.380 |
| Sulfuric Acid | As required for pH 6.85 | As required for pH 6.85 |
| Water For Injection USP | q.s. to 1 mLz | q.s. to 100% | the formulation excluding serum, the electrolytes in the formulation mimicking a physiologic serum amount or concentration.

21. The formulation of claim 20 wherein the osmolality of the formulation is from about 200 to about 500 mOsm/kg.

22. The formulation of claim 20 wherein the osmolality of the formulation is from about 250 to about 400 mOsm/kg.

23. An ophthalmic kit comprising the composition of claim 1 and a means to apply the composition to the eye.

24. An ophthalmic kit comprising the formulation of claim 20 and a means to apply the formulation to the eye.

25. The kit of claim 24 wherein the application means is an eye dropper, an eye cup, an eye spray or gel ointment tube.

26. The kit of claim 25 further comprising a single dose or a multi dose of the formulation in a single container.

27. A method of treating an ocular disease, injury or disorder comprising administering the formulation of claim 1 to a patient in need of such treatment.

28. The method of claim 27 wherein the ocular disease, injury or disorder is caused by surgery, physical damage to the eye, glaucoma, diabetic retinopathy, and/or macular degeneration.

29. The method of claim 28 wherein the ocular disease, injury or disorder is one which results in vascular leakage in the eye or by inflammation in the eye.

30. The method of claim 29 wherein the inflammation in the eye is caused by surgical trauma, dry eye, an allergic, viral, or bacterial infection, injury from a chemical, radiation or thermal burn, or penetration of a foreign body.

31. A method of treating an eye wherein its normal condition has been disrupted or changed comprising administering to the eye the composition of claim 1.

32. A method of treating an eye wherein its normal condition has been disrupted or changed comprising administering to the eye the formulation of claim 20.

* * * * *